United States Patent [19]  [11] Patent Number: 4,511,331
Scebold et al.  [45] Date of Patent: Apr. 16, 1985

[54] CONVERTIBLE BUCCAL TUBE/BRACKET APPLIANCE

[75] Inventors: Robert A. Scebold, Westlake Village; James D. Cleary, Monrovia, both of Calif.

[73] Assignee: Unitek Corporation, Monrovia, Calif.

[21] Appl. No.: 520,957

[22] Filed: Aug. 8, 1983

[51] Int. Cl.³ ............................................... A61C 7/00
[52] U.S. Cl. ........................................... 433/17; 433/8
[58] Field of Search .................................... 433/14, 17

[56] References Cited

U.S. PATENT DOCUMENTS 4,355,975 10/1982 Fujita ................................... 433/17
4,416,627 11/1983 Beasley ................................ 433/17

Primary Examiner—Robert Peshock
Attorney, Agent, or Firm—Stuart E. Krieger; John J. Balser; Isaac Jarkovsky

[57] ABSTRACT

An orthodontic appliance which converts from a buccal tube to a bracket upon the removal of a wire insert which is partly positioned within the longitudinal slot of a bracket body and attached to the surface of the bracket.

2 Claims, 10 Drawing Figures

U.S. Patent Apr. 16, 1985 Sheet 1 of 2 4,511,331
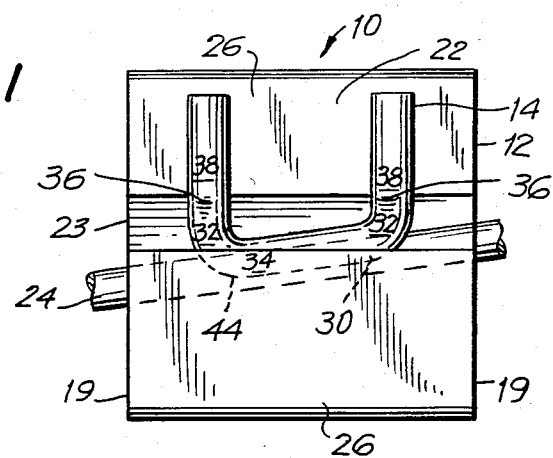
FIG.1
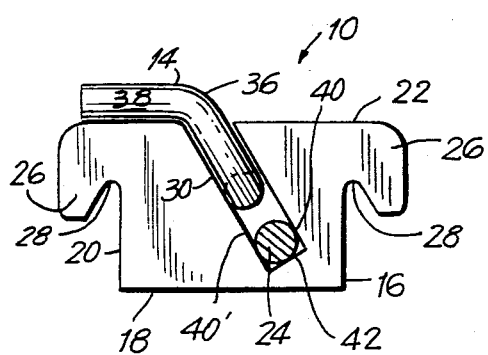
FIG.2
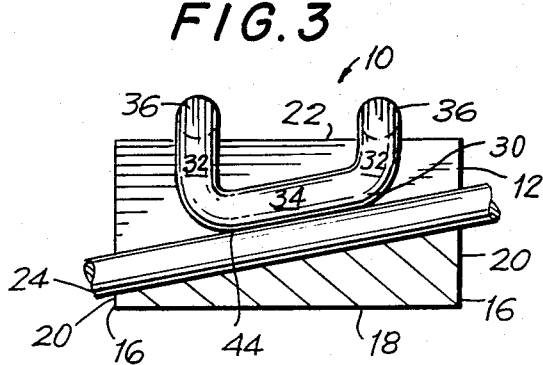
FIG.3
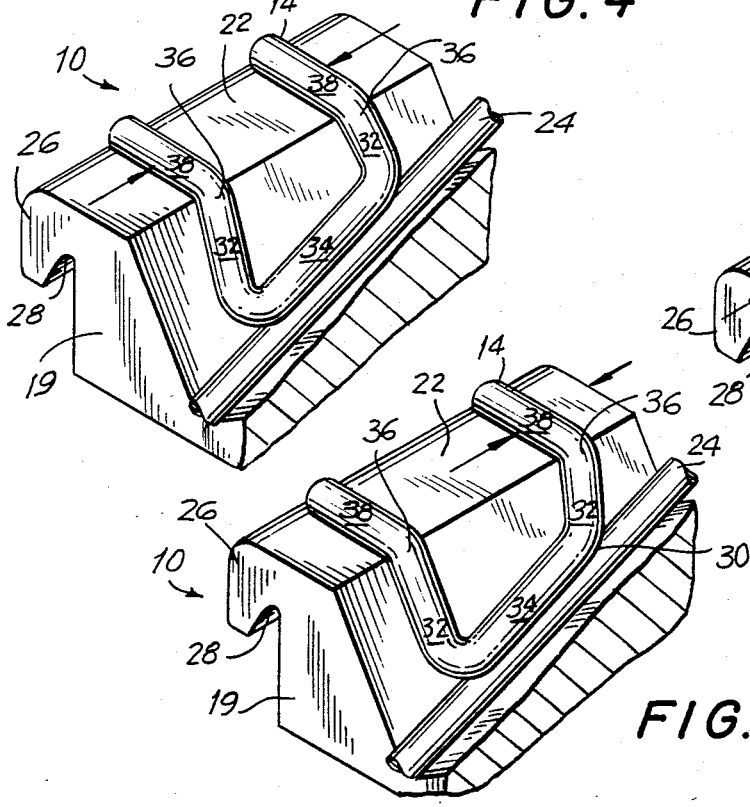
FIG.4
FIG.6
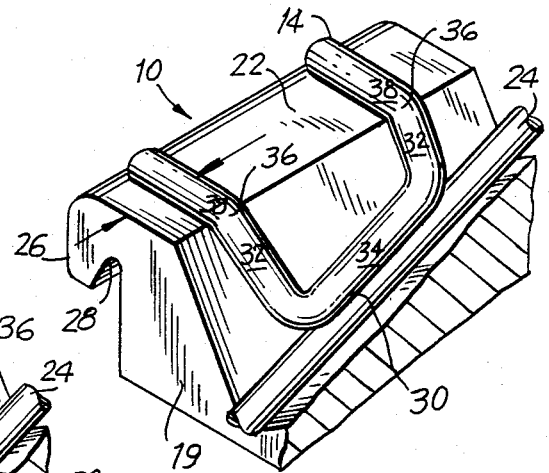
FIG.5

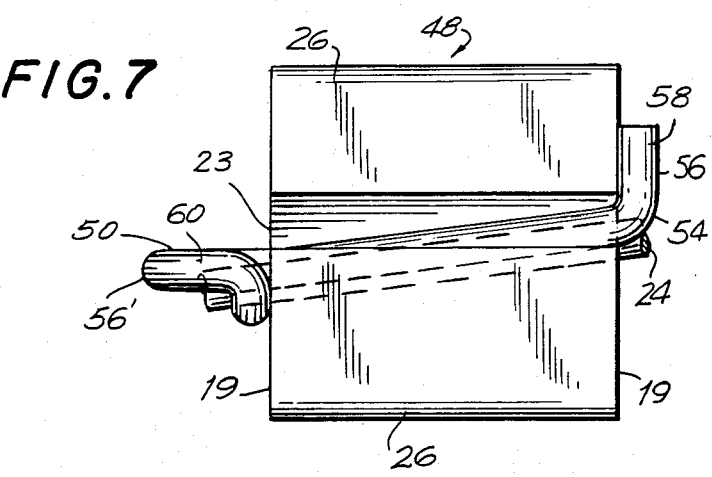
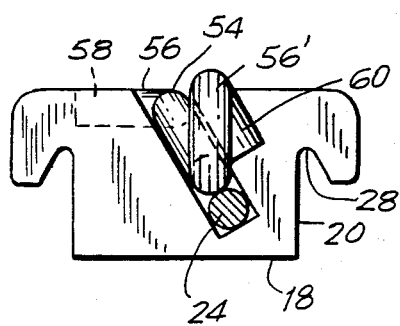
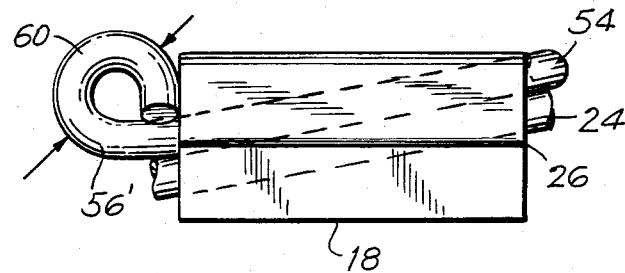
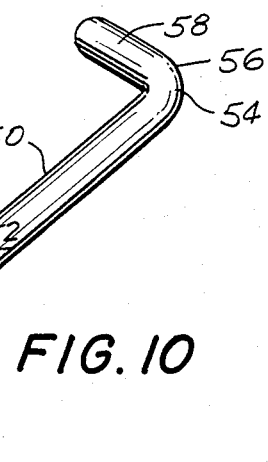

CONVERTIBLE BUCCAL TUBE/BRACKET APPLIANCE

DESCRIPTION

1. Field of the Invention

This invention relates generally to orthodontic appliances and, more particularly, to an orthodontic appliance convertible from a buccal tube to a bracket.

2. Background of the Invention

Buccal tubes are utilized in orthodontic treatment to anchor the opposing ends of the arch wire to the molars. The arch wire is secured, typically by ligature wires intermediate of its ends, to brackets mounted on selected teeth. Appropriate corrective forces are applied to the misaligned teeth via the bracket to properly position the selected teeth with respect to the other teeth in the dental arch.

A buccal tube is attached to each of the two opposing molars by either mounting the tube on a band surrounding the tooth, by welding or soldering, or by directly attaching the buccal tube to the tooth with an adhesive. The arch wire is curved to conform to the dental arch of the patient and each of the wires opposing ends is inserted into a buccal tube which serves as the terminal anchor. This procedure is applicable to both the upper and lower dental arch.

Occasionally, it is necessary in the initial stage of orthodontic treatment to employ a buccal tube on each of the opposing first molars in the dental arch to anchor the arch wire, and in a later stage to utilize a bracket on the first molars, while anchoring the arch wire to buccal tubes mounted on the opposing second molars. This type of orthodontic treatment is usually begun in the patient's childhood. The first or "six year" molars normally serve as the anchor teeth during at least the initial treatment stage and the second molars, which normally appear around age twelve, are used as the anchor teeth in the later stage of the treatment program. Thus, when the second molars appear, the anchoring fixtures are removed from the first molars and anchoring fixtures are added to the second molars.

It has been found desirable in some cases to apply corrective forces to the first molars when they are no longer needed as anchor teeth; however, the earlier conventional anchoring fixtures in place on the first molars did not provide the desired open slot and the wings to accommodate the arch wire and facilitate its attachment to the bracket. The anchoring appliance, therefore, had to be removed from the first molars and raplaced with a conventional arch wire receiving bracket.

This replacement process was uncomfortable for the patient and time consuming for both the patient and dentist. Furthermore, since the molars are in a relatively inaccessible position in the patient's mouth the replacement process was awkward.

Earlier attempts to avoid the replacement process, e.g. as described in U.S. Pat. No. 3,838,514, by utilizing a bracket/buccal tube convertible assembly involved installing a bracket with a plate welded across the bracket slot to form a buccal tube. When the second molars were used as the anchoring teeth, the plate was ground off in the patient's mouth. However, grinding has disadvantages similar to the replacement process, including consumption of time and inconvenience to both dentist and patient.

Other types of removable plates have been attempted; however, difficulties have arisen since the plates have been relatively inaccessible and the mechanical leverage needed to remove the plate from the bracket body has been hard to apply. Furthermore, application of a mechanical force to the plate for the purpose of removal required the application of force vectors to the molars which acted contrary to the corrective force applied during orthodontic treatment.

It is, therefore, an object of the present invention to provide an orthodontic appliance which facilitates conversion from a buccal tube to a bracket assembly without the need for removal of the appliance from the patient's mouth.

It is another object of the present invention to provide an orthodontic appliance which can be converted without applying mechanical forces which are contrary to the corrective forces.

SUMMARY OF THE INVENTION

The present invention comprises an orthodontic appliance which is convertible from a buccal tube into a bracket by the removal of a wire insert. The orthodontic appliance includes the body portion of a conventional bracket having a buccal surface with a mesial-distal longitudinal slot extending therethrough, and a removable wire insert having an intermediate portion and two opposing end portions. The intermediate portion is positioned within the slot so as to form a tubular passageway between the body portion and wire insert; the passageway functioning as a buccal tube capable of accommodating an arch wire therethrough for the purpose of anchorage. The two opposing end portions of the wire insert protrude from the slot so as to be externally accessible and so as to facilitate removal by the application of mechanical force by the dentist.

The wire insert preferably has a planar U-shaped intermediate portion which includes two parallel leg portions interconnected by a bottom portion; and an end or hook portion extending from each of the leg portions. The intermediate, or U-shaped, portion is positioned within the slot and each of the end portions extends from an opposing leg of the U so as to abut the buccal surface of the body portion. The bottom portion of the U-shaped wire insert is distanced from the base of the slot so as to define a passageway therebetween capable of accommodating an arch wire. The end portions are attached to the buccal surface of the bracket body portion typically by welding or soldering. The spatial relationship of the two end portions and opposing vertical bracket sides permits the application of mechanical leverage for the removal of the wire insert from the slot without disrupting the existing orthodontic forces applied to the tooth on which the appliance is mounted.

An alternative wire insert has a substantially straight intermediate portion extending longitudinally through the slot and an end portion extending from opposite sides of the intermediate portion, with each end portion projecting from the slot at the opposing vertical sides of the bracket body. One end portion has a bend or flange which is attached to one of the two substantially vertical bracket surfaces. The other end portion has an attachment flange in the form of a loop with the terminal portion of the loop attached to the other vertical bracket surface.

The term wire insert as used herein includes, but is not limited to, a metallic member having a circular cross-section as occurs in a member formed from a cylindrical rod or a rectangular cross section as occurs when the member is cut from a sheet of metal. The insert is sufficiently strong to insure separation from the bracket as an integral unit.

BRIEF DESCRIPTION OF THE DRAWINGS

The foregoing and other objects, characteristics and advantages of the present invention will be more clearly understood from the following detailed description when read in conjunction with the accompanying drawings in which:

FIG. 1 is a top plan view of a convertible buccal tube/bracket appliance in accordance with the present invention;

FIG. 2 is a left side elevational view of the appliance of FIG. 1;

FIG. 3 is a sectional view taken through the longitudinal slot of the appliance of FIG. 1;

FIG. 4 is a perspective sectional view taken through the longitudinal slot of the appliance shown in FIG. 1 with force vectors appropriate for removal of the wire insert shown by arrows;

FIG. 5 is the same view as FIG. 4 with a second set of force vectors appropriate for removal of the wire insert shown by arrows;

FIG. 6 is the same view as FIG. 5 with a third set of force vectors appropriate for removal of the wire insert shown by arrows;

FIG. 7 is a top plan view of a second embodiment of a convertible buccal tube/bracket in accordance with the present invention;

FIG. 8 is a left side elevational view of the appliance of FIG. 7;

FIG. 9 is a front elevational view of the appliance of FIG. 7, with force vectors appropriate for removal of the wire insert shown by arrows and FIG. 10 is a perspective view of the wire insert used in appliance of FIG. 7.

DESCRIPTION OF THE PREFERRED EMBODIMENT

Referring now to FIGS. 1-6 wherein a convertible buccal tube/bracket orthodontic appliance according to the present invention is shown and generally indicated by the numeral 10. This appliance 10 has a conventional bracket portion 12 and a wire insert 14 secured thereto.

The bracket 12 includes a base 16 having a rear or lingual surface 18 which is adapted to either be secured to a tooth band or directly mounted on the selected tooth, and a body portion 20 with a buccal surface 22 and vertical surfaces 19. The body portion 20 also has a slot 23 extending longitudinally therethrough capable of receiving a conventional arch wire 24 and a pair of overhanging wings 26 located on its opposite lateral edges. The underside of each wing 26 has an inverted U-shaped notch 28.

The wire insert 14 has a U-shaped intermediate portion 30 which includes two opposing leg members 32 and an interconnecting bottom member 34. Each of the leg members 32 has a bend 36 and extending from each bend 36 is an end portion 38. The end portions 38 are welded or otherwise secured to the buccal surface 22 of the bracket body portion 20 intermediate the vertical surfaces 19. The spatial relationship of the end portions 38 relative to the vertical surfaces 19 facilitates removal of the wire insert 14 from the bracket body 20 in the manner shown in FIGS. 4-6 and discussed below.

The longitudinal slot 23 is defined by lateral surfaces 40 and bottom surface 42. The slot 23 has a width and angulation appropriate for the snug accommodation of the arch wire 24 therewithin at the desired orientation for the application of predetermined corrective forces. The length of the insert leg members 32 are chosen so that the interconnecting bottom member 34 parallels and is appropriately spaced from, the bottom surface of the slot 42 so as to define a tubular passageway having dimensions suited for the arch wire 24. A gage pin ground to the dimensions of the tubular passageway can be positioned within the slot 23 prior to the attachment of the wire insert 14 so as to reserve a position in the slot 23, for the arch wire 24. The gage pin is removed from the appliance 10 after the attachment of the insert 14. The passageway is defined by the two lateral slot surfaces 40, 40' bottom slot surface 42 and bottom surface 44 of the interconnecting member 34. When the wire insert 14 is removed, as described below, and the appliance is converted into a convetional bracket 12, the surfaces 40, 40' and 42 of the longitudinal slot 23 provide lateral and bottom support to the arch wire 24. The arch wire 24 may then be further secured to the bracket 12, as is well known in the art so as to reduce movement towards the buccal surface 22 by the application of ligature wires (not shown) tied around the arch wire 24 and overhanging wings 26.

FIGS. 4-6, each of which is a perspective sectional view taken through the center line of the longitudinal slot 23, show three sets of force arrows indicating both the application point and direction of force to be applied by the dental practitioner's tool so as to facilitate removal of the wire insert 14 without upsetting the corrective forces applied to the bracket 12 by the arch wire 24. Equal and opposite forces can be applied in any of the three manners indicated in FIGS. 4-6 by pliers so that the bracket body itself is not disturbed. In FIG. 4, the force arrows show the application of an inwardly directed force from the outside surface of each of the end portions 38. In FIG. 5, the force arrows show application of an outward force from the inner surface of an end portion 28 with the vertical bracket surface 19 serving as a brace. FIG. 6 shows the application of force to the other end portion 38 and vertical surface 19 in a manner similar to that shown in FIG. 5. Since the wire insert 14 has only the end portions 38 secured to the buccal surface 22, the application of forces indicated in the direction of the arrows of FIGS. 4-6 results in detachment of the wire insert 14 and consequent conversion of the appliance 10 from a buccal tube to a bracket 12. It may be necessary in some instances to successively apply the forces as shown in FIGS. 5 and 6 to detach both end portions 38. The wire insert 14 is subsequently removed from the patient's mouth.

An alternative embodiment of the orthodontic appliance is shown in FIGS. 7-10 and generally indicated by the numeral 48. A wire insert 50 consisting of a straight intermediate portion 52 having a bend 54, at each of its ends 56, 56', is secured within a conventional bracket portion 12. Extending from the bend 54, at one end 56, is an end portion which is an attachment flange or hook 58. This flange 58 is welded or otherwise secured to a vertical surface 19 of the bracket body portion 20. Extending from the other end 56' is an end portion which is a helical loop 60 having an outer surface 62. The terminal portion of the helical loop 60 is secured to the vertical surface 19, typically be welding. Preferably, the plane of the loop 60 extends perpendicular to the buccal and lingual surfaces 18 and 22, respectively. In addition, the loop 60 is preferably attached to the mesial vertical surface of the bracket 12. Since brackets are typically mounted on the first molars, accessibility by the dental practitioner is usually increased when the loop is located mesially. The loop facilitates both the gripping by the practitioner's tools, for example a pliers having needle points, and the application of mechanical leverage. Pinching the loop along the force vectors shown by arrows facilitates removal of the wire insert without introducing forces to the tooth.

While the invention has been described above with respect to specific embodiments, it should be clear that these embodiments are given by way of example and shall not be deemed as limiting the scope of the invention, except in accordance with the claims hereof.

We claim:

1. An orthodontic appliance convertible from a buccal tube to a bracket comprising:
 a bracket body portion having opposing vertical surfaces and including a buccal surface having a longitudinal slot extending substantially mesial-distal therethrough; and
 a removable wire insert attached to said body portion having an intermediate portion and two end portions, each extending from an opposing end of said intermediate portion, said intermediate portion extending longitudinally through the length of said slot and being positioned within at least a portion of said slot so as to form a tubular passageway between said body portion and said insert for accommodating an arch wire therethrough, said two opposing end portions protruding from said slot so as to be externally accessible for facilitating removal of said insert, uncovering of said slot and permitting said body portion to be used as a bracket;
 wherein at least one end portion is formed into a helical loop, said loop having a terminal portion attached to a vertical surface.

2. The orthodontic appliance of claim 1 wherein one end portion is a helical loop and said other end portion angularly extends from said intermediate portion and is attached to a vertical bracket body surface.

* * * * *